US007882570B2

(12) United States Patent
Krier

(10) Patent No.: US 7,882,570 B2
(45) Date of Patent: Feb. 8, 2011

(54) INFANT GARMENT

(76) Inventor: Jonelle Krier, 3724 19th Ave. East, Hibbing, MN (US) 55746

( * ) Notice: Subject to any disclaimer, the term of this patent is extended or adjusted under 35 U.S.C. 154(b) by 416 days.

(21) Appl. No.: 11/973,736

(22) Filed: Oct. 10, 2007

(65) Prior Publication Data

US 2009/0099632 A1 Apr. 16, 2009

(51) Int. Cl.
*A41D 11/00* (2006.01)
*A41B 13/08* (2006.01)
(52) U.S. Cl. ................................. 2/80; 2/111
(58) Field of Classification Search ............ 2/69.5, 2/75, 80, 111, 914, 69
See application file for complete search history.

(56) References Cited

U.S. PATENT DOCUMENTS

| 779,809 | A | * | 1/1905 | Sherick ............................ 2/75 |
| 1,117,525 | A | * | 11/1914 | Schlesinger ...................... 2/77 |
| 1,125,467 | A | | 1/1915 | Cannon |
| 1,260,873 | A | * | 3/1918 | Colman ....................... 604/388 |
| 1,365,526 | A | * | 1/1921 | Milkes ........................... 2/270 |
| 1,424,589 | A | * | 8/1922 | Redford ............................ 2/80 |
| 1,435,147 | A | * | 11/1922 | Burns .............................. 2/80 |
| 1,439,502 | A | | 12/1922 | Cahn |
| 1,439,649 | A | * | 12/1922 | Stein ............................. 2/408 |
| 1,758,740 | A | * | 5/1930 | Gale ............................. 2/78.2 |
| 1,813,956 | A | * | 7/1931 | Roberts ............................ 2/80 |
| 2,472,302 | A | * | 6/1949 | Litt et al. .......................... 2/80 |
| 2,524,221 | A | * | 10/1950 | Feeney ............................ 2/80 |
| 2,622,248 | A | | 12/1952 | Schaye |
| D188,893 | S | | 9/1960 | Van Brunt |
| 3,568,213 | A | * | 3/1971 | Mason ............................ 2/80 |
| 3,840,900 | A | * | 10/1974 | Cruz ............................... 2/77 |
| 5,033,121 | A | * | 7/1991 | Larsen .......................... 2/229 |
| 5,125,117 | A | * | 6/1992 | Buenos et al. ................. 2/239 |
| 5,206,957 | A | * | 5/1993 | Gulick ............................ 2/84 |
| 6,339,847 | B1 | | 1/2002 | Hanks |
| 6,668,382 | B1 | | 12/2003 | Wright |
| D512,205 | S | * | 12/2005 | Alexander et al. ........... D2/841 |
| 7,770,237 | B1 | * | 8/2010 | Wright et al. .................. 2/111 |
| 2006/0253953 | A1 | * | 11/2006 | Williams ......................... 2/69 |
| 2009/0031471 | A1 | * | 2/2009 | Dague ............................. 2/83 |

* cited by examiner

*Primary Examiner*—Gary L Welch
*Assistant Examiner*—Amber R Anderson
(74) *Attorney, Agent, or Firm*—Patterson Thuente Christensen Pedersen, P.A.

(57) ABSTRACT

An infant garment preserves body heat and facilitates access to a localized region of the body surface of a patient. The garment has a slit on the front that allows the region of the patient's body surface to be monitored and, if necessary, treated without requiring removal of the garment. The garment also has sleeves with cuffs that can be reversibly folded to cover or uncover the hand-openings in the distal ends of the sleeves.

17 Claims, 3 Drawing Sheets

INFANT GARMENT

FIELD OF THE INVENTION

The present invention relates to patient garments. More specifically, the present invention relates to garments for preserving an infant's body heat and facilitating access to a localized region of the body surface of a patient.

BACKGROUND OF THE INVENTION

Around the beginning of the twentieth century, most women gave birth at home. As modern hospitals gained popularity during the 1920s, women were encouraged to seek professional health care for themselves and their newborns in the supervised environments of these new hospitals. By 1936, approximately one-third of all live births occurred in hospitals, and by 1945, approximately eighty percent of women gave birth in hospitals. Although tremendous advances have been made in the field of medicine, hospital apparel—including infant garments—has changed little.

For years, the traditional infant garment has been a short shirt ending at the waistline. Typically, some type of undergarment, such as a diaper, has also been used for additional protection against soiling. The short shirt is open in the front with two side panels crossing over one another for closing and fastening the shirt shut. Early shirts were shut in the back with ties. These ties were later replaced with snap fasteners. The short shirt allows a cloth diaper to be used, thereby decreasing the possibility of soiling the upper garment and reducing the frequency of laundering. Although rubber or plastic pants can also be used with short shirts, their use has typically been discouraged because they can contribute to improper air circulation and increased susceptibility to the development of rashes.

Another type of traditional undergarment for infants is the undershirt. Undershirts for newborns have front tabs that can be fastened to a cloth diaper with safety pins. This forms a full-length, warm, cloth garment that can be secured in place so as to not ride up on the infant. As disposable diapers were slowly introduced into nurseries in the late 1970s, however, the front tabs have been omitted since potentially hazardous safety pins were no longer necessary.

Currently, hospital garments for infants have the same waist-length undershirt with cross-over front panels that snap shut. Such garments typically require the use of a separate, disposable diaper. A drawback of these types of garments is that crossing the front panels over and snapping them shut can be confusing and cumbersome. Since the garment is separate from the diaper, another drawback of the infant garment commonly in use today is that the shirt may tend to ride up under the infant's armpits. This unnecessarily exposes portions of the surface of an infant's body and can contribute to a loss of body heat.

Since the body temperatures of infants should normally be maintained within a very narrow range, the effects of heat loss on infants can be especially dangerous. Excessive heat loss stemming from the use of existing infant garments can, for example, contribute to the onset of hypothermia. As a result, newborn care, policies, and techniques attempt to thermo-regulate the body of newborns by achieving a healthy and an efficient balance between heat loss and heat production. Because the garments worn by infants sometimes may not always effectively maintain a proper body temperature, however, it can become necessary to expend significant resources to create appropriate temperature-controlled neonatal environments.

Another drawback of current hospital garments is that they can impede patient care. Specifically, the garment itself can impede access to various locations on an infant's body which may require monitoring or treatment. Current standards of patient care, however, emphasize the responsibility of hospital personnel to easily assess patients and quickly identify real and potential problems.

Therefore, there is a need in the industry for hospital garments, especially garments for infants, that more effectively preserve body heat while providing improved access for the assessment and care of the patient wearing the garment.

SUMMARY OF THE INVENTION

The apparatuses and methods according to the various embodiments of the present invention provide thermo-regulating infant garments. The thermo-regulating infant garments generally present an opening that provides accessibility for assessing a physical condition or parameter or caring for a wound site. The wound site may be, for example, the site of a post-birth resection of the umbilical cord, an introduction of an intra-venous tube or a needle, a surgical incision, or other physical injury. The physical condition or parameter may be, for example, heart rate, respiration, or the functioning of the bowels.

When worn by a patient, the garment of the present invention helps retain the patient's body heat. A desired region of the patient's body surface can also be accessed and for assessing a physical condition and, if necessary, providing treatment. A slit in the garment allows such assessment and treatment without requiring the garment to be removed. In addition, a cuff sewn onto the distal end of a sleeve of the garment can be folded so as to selectively cover or uncover the open, distal end of the sleeve. Covering the open, distal end of the sleeve can thereby cover the hand-opening of the sleeve to reduce the risk of self-inflicted injury and further retain body heat.

The present invention is generally described in relation to embodiments of garments for neo-natal babies. Alternative embodiments could easily be adapted for use by adults, however, without departing from the spirit or scope of the present invention.

In an embodiment of the present invention, a thermo-regulating infant garment provides access to an umbilical region of a patient and includes (i) a torso cover having a front and a back and defining a head opening, two spaced-apart arm openings, and a bottom opening, (ii) a pair of rollable sleeves having a proximal end and a distal end, the proximal end being attached to the torso cover at the arm openings and the distal end defining a hand opening and forming a cuff, and (iii) a flap intermediate the front and the back of the torso cover and opposite the head opening. The flap is attachable to the torso cover to at least partially cover the bottom opening. The front of the torso cover has a bottom edge and defines a slit extending from the bottom edge. The cuff is reversibly foldable over the hand opening.

BRIEF DESCRIPTION OF THE DRAWINGS

The embodiments of the present invention may be more completely understood in consideration of the following detailed description of various embodiments of the invention in connection with the accompanying drawings, in which.

Figure 1:
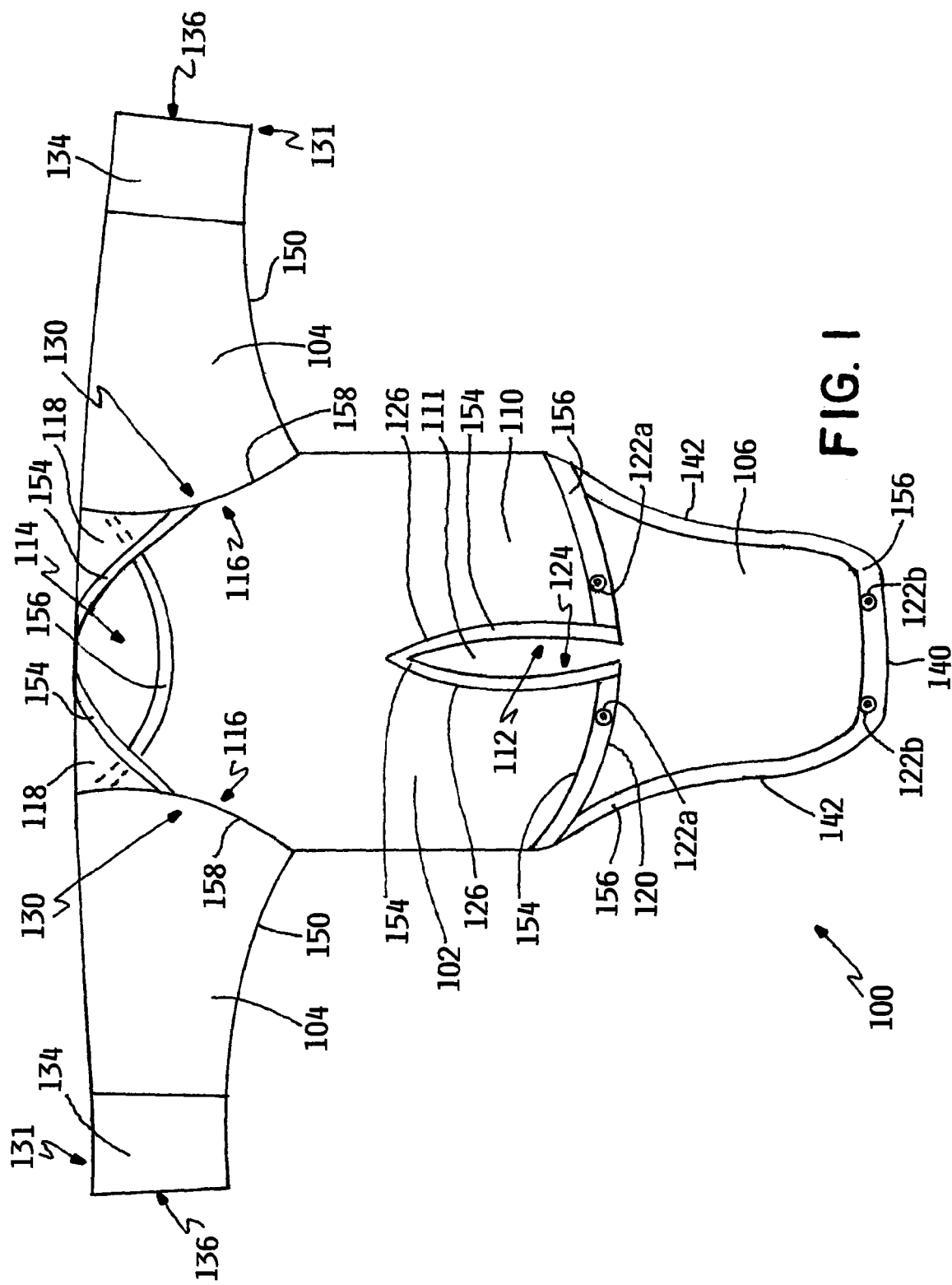
FIG. 1 is a front view of an infant garment according to an embodiment of the present invention.

While the present invention is amendable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention as defined by the appended claims.

DETAILED DESCRIPTION OF THE EMBODIMENTS

The garment of the present invention can be used in a variety of applications, including as hospital and non-hospital garments for children and adults. The garment is particularly advantageous for use as an infant garment, however. Accordingly, the present invention is described by way of example in connection with, but is not limited to, a neo-natal infant garment, as indicated generally at garment 100 in FIG. 1. It should be understood that garment 100 of the present invention is not in any way limited to such use and can be applied to a variety of other garments, such as garments for toddlers and adults.

Referring to FIG. 1, garment 100 according to an embodiment of the present invention includes torso cover 102, sleeves 104, and pelvic flap 106. Torso cover 102 generally has front 110, back 111, patient-assessment opening 112, head opening 114, armpit regions 116, and shoulder regions 118. Torso cover 102 may also have a hood (not shown). Generally, overlapping portions of front 110 and back 111 of torso cover 102 define head opening 114 and shoulder regions 118. Lower edge 120 of front 110 of garment 100 generally has fastening members 122a. In an example embodiment, pelvic flap 106 of garment 100 is attachable to front 110 of torso cover 102.

Figure 3:
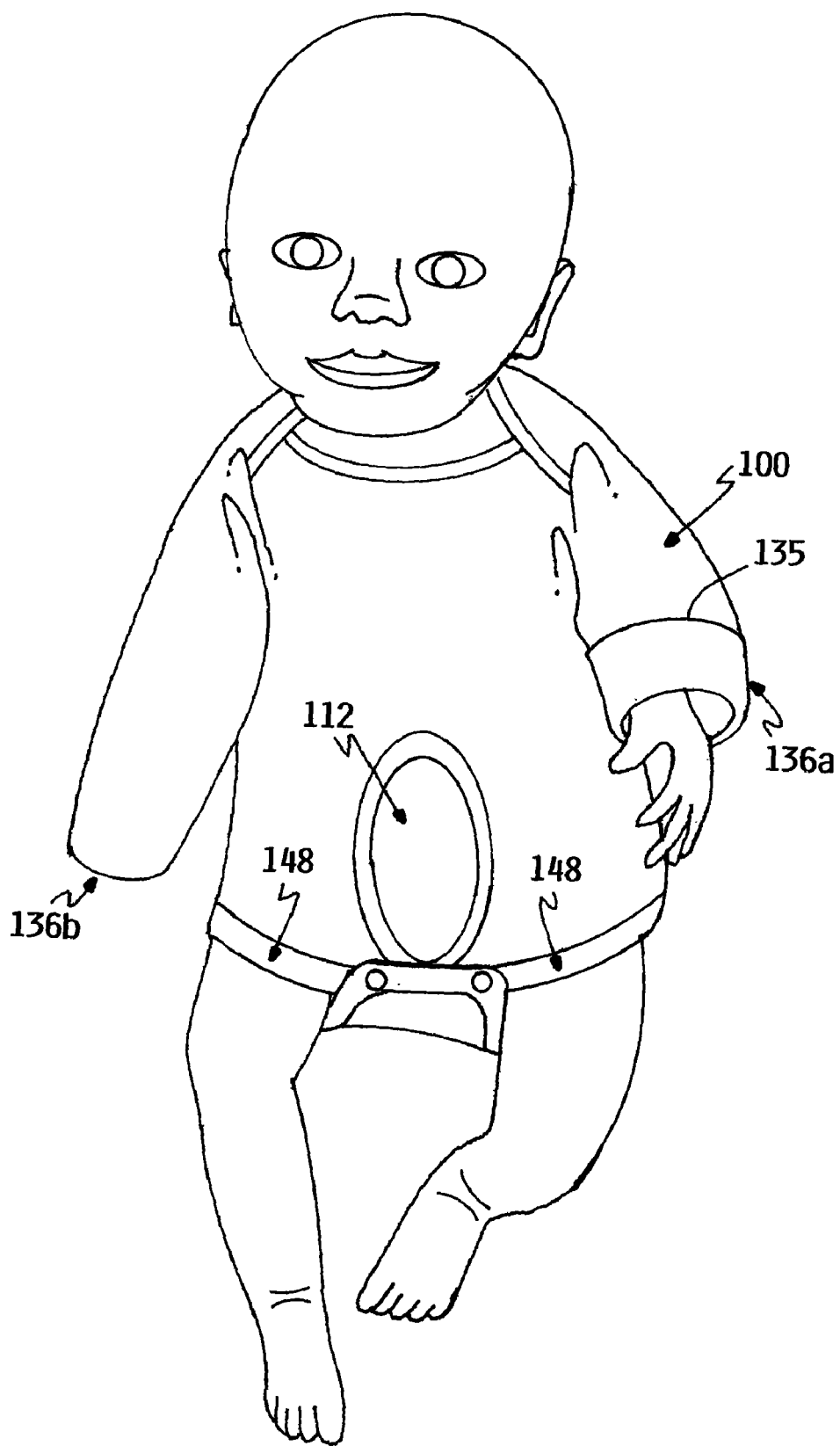
FIG. 3 is a perspective view of an infant garment according to an embodiment of the present invention presented on the body of an infant.

Patient-assessment opening 112 permits a portion of the body of a user wearing garment 100 to be accessed. Patient-assessment opening 112 facilitates such access without requiring garment 100 to be removed or pelvic flap 106 to be detached from front 110 of torso cover 102. In an example embodiment, patient-assessment opening 112 is positioned on garment 100 so that the umbilical or lower abdominal region of a user wearing garment 100 can be accessed, as depicted in FIG. 3. Patient-assessment opening can also be positioned on garment 100 so that a different region of the patient's body can be accessed. This allows a particular condition or parameter to be monitored or assessed while decreasing the disturbance normally caused by repositioning garment worn by a patient. In an alternative embodiment, patient-assessment opening 112 is positioned on garment 100 so that heart, lungs, or bowels of a patient can be monitored, such as, for example, with a stethoscope.

Patient-assessment opening 112 may be any number of types of openings that would permit an area of a patient's body, such as the umbilical or lower abdominal region, to be monitored. Generally, patient-assessment opening 112 defines slit 124. In an example embodiment, slit 124 is in front 110 of garment 100 and runs from lower edge 120 toward head opening 114. Slit 124 can be between approximately one inch and eight inches in length. In an example embodiment, slit 124 is approximately four-and-one-half inches in length. One skilled in the art will readily recognize that patient-assessment opening 112 may have a configuration other than slit 124 and/or be located in an area other than front 110 of garment 100 running from lower edge 120 toward head opening 114 without departing from the spirit of scope of the present invention.

Referring to FIG. 1, slit 124 has slit edges 126. In an example embodiment, slit edges 126 are not fastenable or overlapping. Patient-assessment opening 112 thereby remains open in an example embodiment, as depicted in FIG. 3. In an alternative embodiment, slit edges 126 may have fastening members so that patient-assessment opening 112 may be closed.

Each sleeve 104 has proximal end 130, distal end 131, anterior side 132, and posterior side 133. Proximal end 130 is contoured so as to define a shape complementary to armpit regions 116 of torso cover 102, as depicted in FIG. 1. Distal end 131 has cuff 134 with cuff edge 135. Distal end 131 also defines hand opening 136. Hand opening 136 is generally large enough and positioned on sleeve 104 so as to be able to receive the hand of an individual wearing garment 100. Generally, cuff 134 occupies only a portion of distal end 131. For example, cuff 134 may be located on the anterior side 132 or posterior side 133 of sleeve 104, but generally does not extend around the circumference of distal end 131 of sleeve 104. The portion of sleeve 104 that has cuff 134 therefore generally has more layers of fabric material than the portion of sleeve 104 that does not have cuff 104.

Figure 2:
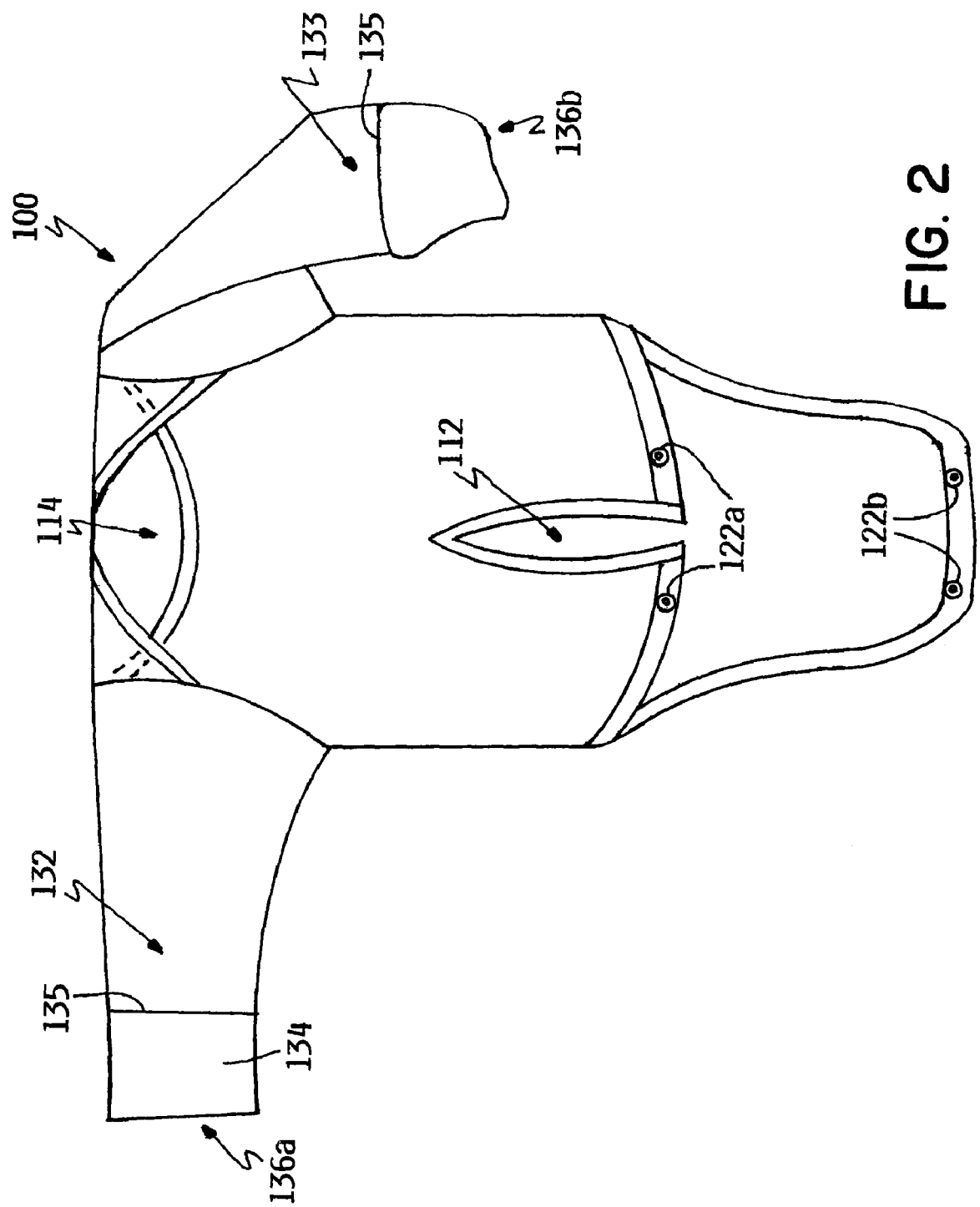
FIG. 2 is a front view of an infant garment according to an embodiment of the present invention having a sleeve folded over itself.

Cuff 134 can be folded over distal end 131 of sleeve 104 to cover or uncover hand opening 136. Sleeve 104 having uncovered hand opening 136a and sleeve 104 having covered hand opening 136b are depicted in FIG. 3. In an example embodiment, cuff 134 is positioned on anterior side 132 of sleeve 104 having uncovered hand opening 136a and is positioned on the posterior side 133 of sleeve 104 having covered hand opening 136b, as depicted in FIG. 3. Accordingly, cuff edge 135 can be viewed on anterior side 132 of sleeve 104 having uncovered hand opening 136a, but cannot be viewed on anterior side 132 of sleeve 104 having covered hand opening 136b. In an alternative embodiment, cuff 134 is positioned on anterior side 132 of sleeve 104 having covered hand opening 136b and is positioned on posterior side 133 of sleeve having uncovered hand opening 136a, as depicted in FIG. 2. Accordingly, cuff edge 135 can be viewed on anterior side 132 of sleeve 104 having covered hand opening 136b, and can also be viewed on posterior side 133 of sleeve 104 having uncovered hand opening 136b. By having cuff 134 that can be selectively folded and unfolded, sleeves 104 of garment 100 can be quickly and easily modified to cover the hands of an individual wearing garment 100, such as, for example, an infant.

Pelvic flap 106 has bottom edge 140 and side edges 142. Bottom edge 140 has fastening members 122b. Generally, fastening members 122b on bottom edge 140 of pelvic flap 106 function in concert with fastening members 122a of lower edge 120 of front 110 of torso cover 102. Fastening members 122a,b can be any number of fastening members that facilitate the attachment of bottom edge 140 of pelvic flap 106 to lower edge 120 of torso cover 102. In an example embodiment, fastening members 122a,b are snaps. In alternative embodiments, fastening members 122a,b are zippers, button-and-eye fasteners, or hook-and-loop fasteners.

Pelvic flap 106 of garment 100 can have any numbers of shapes and sizes. In an example embodiment, pelvic flap 106 is shaped so that, when attached to torso cover 102, pelvic flap 106 and torso cover 102 form leg openings 148, but otherwise substantially cover an individual below his or her umbilical region, as depicted in FIG. 3. For example, side edges 142 may have a convex shape when pelvic flap 106 is not attached to torso cover 102, as depicted in FIG. 1. Referring to FIG. 3, the legs of an individual wearing garment 100 can be extended through leg openings 148 when pelvic flap 106 is attached to torso cover 102. In an alternative embodiment, bottom edge 140 and side edges 142 of pelvic flap 106 are shaped so to not form an opening when pelvic flap 106 is attached to torso cover 102. In this alternative embodiment, pelvic flap 106 generally defines a pair of apertures (not shown) through which the legs of an individual wearing garment 100 can be extended.

Sleeves 104 and pelvic flap 106 may be attached to torso cover 102 in any number of ways. In an example embodiment, sleeves 106 are separate from torso cover 102 and pelvic flap 106. In accordance with this embodiment, sleeves 104 are generally sewn onto torso cover 102, as depicted in FIGS. 1-2. In an alternative embodiment, sleeves 104, pelvic flap 106, and torso cover 102 constitute the same piece of fabric material. In accordance with this embodiment, a single shape can be cut out from a roll of fabric material such that the cut material forms garment 100 when folded over itself and sewn together. In another embodiment, sleeves 104, pelvic flap 106, and torso cover 102 are all formed from separate pieces of material.

Garment 100 may be made from any number of materials and in any number of ways. Referring to FIG. 1, torso cover 102 and pelvic flap 106 generally form a single piece of material, while sleeves 104 form separate pieces of material. Sleeves 104 and torso cover 102 and pelvic flap 106 can be made from tubular or non-tubular fabric that is sewn together. In an example embodiment, sleeve material is sewn along seam 150 to form sleeve 104 having cuff 134, while torso cover 102 and pelvic flap 106 are formed from tubular fabric. Generally, back 111 is cut higher than front 100. An elongated back 111 can then be folded toward front 110 to create shoulder regions 118.

In an alternative embodiment, torso cover material and lower portion material is sewn along seams (not shown) to form torso cover 102 and pelvic flap 106. Torso cover 102 and pelvic flap 106 can also be sewn so as to have seam bindings 154, 156, as depicted in FIG. 1. In an example embodiment, seam bindings 154, 156 are formed by folding a separate piece or pieces of fabric material over the edges of garment 100 and sewing the separate piece or pieces. In an alternative embodiment, seam bindings 154, 156 are formed by folding over and sewing the edges of fabric material, such as, for example, bottom edge 140 of pelvic flap 106 and lower edge 120 of front 110 of garment 100.

In example embodiment, sleeves 104 are attached to armpit regions 116 of torso cover 102 along attachment seams 158. Although FIGS. 1-3 depict garment 100 constructed from torso cover 102, sleeves 104, and pelvic flap 106 cut in a particular pattern, it will be apparent to one skilled in the art that any number of shapes can be cut from fabric material so as to form garment 100. For example, in an alternative embodiment, torso cover 102 and pelvic flap 106 are separate, individual components.

Generally, all components of garment 100 are made from the same materials. In an example embodiment, garment 100—other than fastening members—is made substantially from an elastic cotton knit. Seam bindings 154, 156 and garment 100 can be made from the same or different material and can have the same or different weaves. In an example embodiment, seam bindings 154, 156 are made from the same material as garment 100, but have a tighter weave per square inch than garment 100. In an alternative embodiment, garment 100—other than fastening members—is made from a non-cotton material.

In operation, garment 100 can be worn by an individual to reduce the loss of body heat while providing an access point to the umbilical region of the individual. Specifically, an individual's arms can be inserted through sleeves 104 and the individual's head can be inserted through head opening 114 of torso cover 102. Pelvic flap 106 is drawn between the legs of the individual from back 111 of torso cover 104 toward front 110 of torso cover 102. To maintain pelvic flap 106 in place, fastening members 122b on bottom edge 140 of pelvic flap 106 are secured to fastening members 122a on lower edge 120 of front 110 of garment 100.

With garment 100 secured around the individual, the area of the individual's body exposed by the patient-assessment opening 112 can be monitored and/or cared for. In an example embodiment, patient-assessment opening 112 allows the site at which the umbilical cord was resected from a neo-natal baby to be monitored and/or be cared for.

Garment 100 can also be used to cover the hands of an individual wearing garment 100. Specifically, cuff 134 can be folded over hand opening 136 of sleeve 104 so as to cover hand opening 136. Cuff 134 can also be folded back over hand opening 136 of sleeve so as to uncover hand opening 136. In an example embodiment, hand opening 136 is covered by folding cuff 134 from anterior side 132 of sleeve 104 to posterior side 133 of sleeve 104, while hand opening 136 is uncovered by folding cuff 134 from posterior side 133 of sleeve 104 to anterior side 132 of sleeve 104. In an alternative embodiment, hand opening 136 is covered by folding cuff 134 from posterior side 133 of sleeve to anterior side 132 of sleeve 104, while hand opening 136 is uncovered by folding cuff 134 from anterior side 132 of sleeve 104 to posterior side 133 of sleeve 104.

The embodiments above are intended to be illustrative and not limiting. Additional embodiments are within the claims. In addition, although the present invention has been described with reference to particular embodiments, those skilled in the art will appreciate that changes can be made in form and detail without departing from the spirit and scope of the present invention. Any incorporation by reference of documents above is limited such that no subject matter is incorporated contrary to the explicit disclosure herein.

What is claimed:

1. A thermo-regulating garment that provides access to an umbilical region of an infant wearing the garment, the garment comprising:

a torso cover having a front and a back, the torso cover defining a head opening, two arm openings, and a bottom opening, and the front having a bottom edge;

a pair of foldable sleeves having a proximal end and a distal end, the proximal end being attached to the torso cover at the arm openings and the distal end defining a hand opening;

a flap intermediate the front and the back of the torso cover and opposite the head opening, the flap being attachable to the bottom edge of the torso cover to at least partially cover the bottom opening; and a patient-assessment opening in the front of the torso cover defining a slit centrally located in the front of the torso cover having a first slit edge and a second slit edge that do not overlap, the first and second slit edges diverging before converging at an end point located prior to the neck opening as the first and second slit edges extend in the longitudinal direction away from the bottom edge towards the head opening, and the slit having a vertical length between 1 and 8 inches from the bottom edge to the end point;

wherein the patient-assessment opening provides access to the umbilical region of the infant wearing the thermo-regulating garment when the flap is fully attached to the bottom edge of the front of the torso cover.

2. The garment of claim 1, wherein the flap is attachable to the bottom edge of the front of the torso cover by at least one fastening member selected from the group consisting of a snap, a zipper, a button-and-eye fastener, and a hook-and-loop fastener.

3. The garment of claim 2, wherein the flap forms a pair of leg openings in the bottom opening when attached to the bottom edge of the front of the torso cover.

4. The garment of claim 3, wherein the flap and the front and back of the torso cover are shaped such that the leg openings are substantially circular when the flap is attached to the bottom edge of the front of the torso cover.

5. The garment of claim 2, wherein the flap attaches to the bottom edge of the front of the torso cover, and wherein the at least one fastening member are snaps.

6. The garment of claim 2, wherein the flap defines a pair of leg openings.

7. The garment of claim 2, wherein the flap is integral to the back of the torso cover.

8. The garment of claim 7, wherein the torso cover and the flap are constructed from a substantially tubular fabric material.

9. The garment of claim 2, wherein the flap and the bottom edge of the front of the torso cover have a fastening member for selectively attaching the flap to the bottom edge of the front of the torso cover.

10. The garment of claim 2, wherein the slit is also capable of remaining substantially open to provide access to the umbilical region of the patient wearing the thermo-regulating garment when the flap is partially attached to the front of the torso cover.

11. The garment of claim 1, wherein the slit exposes the umbilical region and provides access to at least a portion of a chest region of the patient.

12. The garment of claim 11, wherein the material is an elastic cotton knit.

13. The garment of claim 1, wherein each sleeve further defines an anterior side and a posterior side, the distal end of each sleeve having a cuff located on the posterior side, the cuff on each sleeve capable of being selectively folded and unfolded over the respective hand opening.

14. The garment of claim 1, wherein each sleeve further defines an anterior side and a posterior side, the distal end of each sleeve having a cuff located on the anterior side, the cuff on each sleeve being capable of being selectively folded and unfolded over the respective hand opening.

15. The garment of claim 1, wherein the torso cover, the sleeves, and the flap are made from a same material.

16. The garment of claim 1, wherein the torso cover is constructed from a substantially tubular fabric material.

17. The garment of claim 1, wherein the distal end of the pair of foldable sleeves forms a cuff, the cuff on the pair of foldable sleeves is reversibly foldable over the hand opening.

* * * * *